United States Patent
Sinquin et al.

(10) Patent No.: US 8,183,192 B2
(45) Date of Patent: *May 22, 2012

(54) LUBRICATING OIL ADDITIVE AND LUBRICATING OIL COMPOSITION CONTAINING SAME

(75) Inventors: Gilles P. Sinquin, Saint Martin Du Manoir (FR); Michael R. Adams, Richmond, CA (US)

(73) Assignees: Chevron Oronite Company LLC, San Ramon, CA (US); Chevron Oronite S.A., Cedex (FR)

( * ) Notice: Subject to any disclaimer, the term of this patent is extended or adjusted under 35 U.S.C. 154(b) by 239 days.

This patent is subject to a terminal disclaimer.

(21) Appl. No.: 12/658,120

(22) Filed: Feb. 3, 2010

(65) Prior Publication Data

US 2011/0190185 A1 Aug. 4, 2011

(51) Int. Cl.
*C10M 159/22* (2006.01)
(52) U.S. Cl. .................................... 508/574; 508/586
(58) Field of Classification Search .................. 508/574, 508/391, 586; 568/716, 75; 526/351
See application file for complete search history.

(56) References Cited

U.S. PATENT DOCUMENTS

| | | | |
|---|---|---|---|
| 2,360,302 A | 10/1944 | Etzler et al. | |
| 2,592,428 A | 4/1952 | Kemp et al. | |
| 2,680,096 A | 6/1954 | Walker et al. | |
| 2,814,655 A | 11/1957 | Langlois et al. | |
| 3,178,368 A | 4/1965 | Hauneman | |
| 3,368,972 A | 2/1968 | Otto | |
| 3,388,063 A | 6/1968 | Allphin, Jr. | |
| 3,429,812 A | 2/1969 | Kivelevich | |
| 3,649,229 A | 3/1972 | Otto | |
| 3,801,507 A | 4/1974 | Henrickson et al. | |
| 3,887,634 A | 6/1975 | Hughes | |
| 4,157,309 A | 6/1979 | Wilgus et al. | |
| 4,435,601 A | 3/1984 | Formanek et al. | |
| 5,281,346 A | 1/1994 | Adams et al. | |
| 5,370,805 A | 12/1994 | Smrcka et al. | |
| 5,458,793 A | 10/1995 | Adams et al. | |
| 5,510,043 A | 4/1996 | Inoue | |
| 5,570,043 A | 10/1996 | Churchill | |
| 5,759,966 A | 6/1998 | Campbell | |
| 6,340,659 B1 | 1/2002 | Kucsis et al. | |
| 6,372,696 B1 | 4/2002 | Tipton | |
| 2005/0288194 A1 | 12/2005 | Small et al. | |
| 2007/0049508 A1 | 3/2007 | Stonebraker et al. | |
| 2010/0029527 A1* | 2/2010 | Campbell et al. | 508/567 |

FOREIGN PATENT DOCUMENTS

| | | |
|---|---|---|
| EP | 1 760 135 | 3/2007 |
| GB | 734605 | 9/1955 |
| GB | 734622 | 9/1955 |

OTHER PUBLICATIONS

U.S. Appl. No. 12/221,171, filed Jul. 31, 2008, Campbell et al.
Ambient Aquatic Life Water Quality Criteria for Nonylphenol-Draft, United States Environmental Protection Agency, Office of Water 4304T, EPA 822-R-03-029, Dec. 2003, pp. 1-71, www.epa.gov/waterscience/criteria/nonphenol.
Watanabe et al., Tissue-specific estrogenic and non-estrogenic effects of a xenoestrogen, nonlyphenol, Journal of Molecular Endocrinology, (2004), pp. 243-252, vol. 33, 2004 Society of Endocrinology, Printed in Great Britain, 0952-5041/04/033-243, www.indocrinology.org.
Tabira et al., Structural requirements of para-alkylphenols to bind to estrogen receptor, Eur. J. Biochem (1999) pp. 240-245, vol. 262, FEBS 1999.
Routledge et al., Structural Features of Alkylphenolic Chemicals Associated with Estrogenic Activity, The Journal of Biological Chemistry, 1997, pp. 3280-3288, vol. 272, No. 6, Issue of Feb. 7, 1997 by the American Society for Biochemistry and Molecular Biology, Inc., www-jbc.standford.edu/jbc/.
Alkylphenols & Ethoxylates Research Council, Alkylphenols and Alkylphenol Ethoxylates, an Overview of Safety Issues, Jan. 1999, APE Research Council: White Paper, pp. 1-9, www.aperc.org/docs/whitepaper-overview.html.
George et al., Final Report, Assessment of Pubertal Development and Thyroid Function in Juvenile Female CD® (Sprague-Dawley) Rats After Exposure to Selected Chemicals Administered by Gavage on Postnatal Days 22 to 42/43, RTI Identification No. 65U-08055.001.015.002, RTI Protocol No. RTI-830, pp. 1-52, www.epa.gov/scipoly/oscpendo/assayvalidation/status.html, Mar. 28, 2005.

* cited by examiner

*Primary Examiner* — Ellen McAvoy
*Assistant Examiner* — Vishal Vasisth

(57) ABSTRACT

An overbased salt of an oligomerized alkylhydroxyaromatic compound for use in a lubricating oil composition is disclosed, wherein the alkyl group of the alkylhydroxyaromatic compound is derived from an olefin mixture comprising propylene oligomers having an initial boiling point of at least about 195° C. and a final boiling point of greater than 325° C. and up to about 400° C. as measured by ASTM D86. Also disclosed is a propylene oligomer having an initial boiling point of at least about 195° C. and a final boiling point of greater than 325° C. and up to about 400° C. as measured by ASTM D8, wherein the propylene oligomer contains a distribution of carbon atoms that comprise at least about 50 weight percent of $C_{14}$ to $C_{20}$ carbon atoms.

18 Claims, No Drawings

LUBRICATING OIL ADDITIVE AND LUBRICATING OIL COMPOSITION CONTAINING SAME

BACKGROUND OF THE INVENTION

1. Technical Field

The present invention generally relates to a propylene oligomer, a lubricating oil additive derived from the propylene oligomer, and lubricating oil composition containing same.

2. Description of the Related Art

There is increasing evidence that certain synthetic and natural chemicals may act on the endocrine system. For example, certain synthetic and natural chemicals can act as agonists or antagonists to cellular receptors such as estrogen receptors, androgen receptors, and thyroid hormone receptors. Agonists bind to cellular receptors and trigger a response, whereas antagonists block the action of an agonist. Natural and synthetic chemicals can interfere in various ways with naturally occurring hormones. These chemicals can be called endocrine disruptors. For example, endocrine disruptors can (1) mimic naturally occurring hormones by binding to hormone receptors, (2) block the binding of naturally occurring hormones to their respective hormone receptors, (3) alter natural levels of hormones, (4) increase or decrease natural hormone levels, and (5) interfere with the way hormones travel through the body.

Chemicals that interfere with the normal functioning of estrogens and estrogen receptors provide an example of endocrine disruptors. Certain chemicals (called pseudo-estrogens) and natural estrogens can share a common mechanism of action. In normal cases, estrogenic activity is produced by binding natural estrogen to an estrogen receptor (ER) within the nucleus of the cell, followed by transcriptional activation of target genes. This transcriptional activation can occur through the binding of the estrogen receptor to promoter sequences within the regulatory region of the target genes. When endocrine disruptors are present that mimic natural estrogens, the endocrine disruptor can bind to the ER causing transcriptional activation by the ER even though no natural estrogen is present. Similarly, antiestrogenic activity is produced by endocrine disruptors which bind to ERs, but which do not subsequently activate the occupied ER as well as natural estrogen. Finally, selective estrogen receptor modulators (SERMs) bind to ERs, but subsequently activate cellular responses that differ from those activated by the natural estrogens. In general, all but a very small number of molecules that bind to ERs produce some activation of the receptors, as either estrogens or as SERMs.

Alkylphenols and products produced from them have come under increased scrutiny due to their association as potential endocrine disruptive chemicals. This is due to the weak estrogenic activity of alkylphenols as well as degradation intermediates of the alkylphenol products. Alkylphenols are commercially used in, for example, herbicides, gasoline additives, dyestuffs, polymer additives, surfactants, lubricating oil additives and antioxidants. In recent years, alkylphenol alkoxylates, such as ethoxylated nonylphenol, have been criticized for having poor biodegradability, high aquatic toxicity of the by-products of the biodegradation of the phenol portion. Thus, there is an increasing concern that these chemicals may act as endocrine disrupters, for example, by acting as pseudo-estrogens. Some studies have shown there to be a link between alkylphenols and declining sperm count in human males and there is evidence that alkylphenols may harmfully disrupt the activity of human estrogen and androgen receptors. Specifically, Routledge et al., "Structural features of alkylphenolic chemicals associated with estrogenic activity", J Biol. Chem., 1997 Feb. 7; 272(6):3280-8,. compared the estrogenic activity of different alkylphenols with the naturally occurring hormone 17β-estradiol in an estrogen-inducible strain of yeast. The results indicated that optimal estrogenic activity requires a single branched alkyl group composed of between 6 and 8 carbon atoms located at the para position on an otherwise unhindered phenol ring with 4-tert-octylphenol (8 carbons also named 4-(1,1,3,3-Tetramethylbutyl)-phenol)) having the highest activity. Routledge et al. tested various alkylphenols in the assay and indicated that alkyl chain length, degree of branching, location of the alkyl group on the phenyl ring, and degree of isomeric heterogeneity affect the binding efficiency but they were not able to draw a structure activity conclusion. For example, Routledge et al. speculated that the isomers of p-nonylphenol, which was identified to have 22 para-isomers as determined by high resolution gas chromatographic analysis, would not have similar activity. Routledge et al., however, did not elucidate which isomer or isomers were the active species. Interestingly, Tabria et al., "Structural requirements of para-alkylphenols to bind to estrogen receptor", Eur. J. Biochem. 262, 240-245 (1999) found that when using human estrogen receptors, the receptor binding of alkylphenols was maximized when the number of alkyl carbons was nine carbon atoms. Tabria et al. noted that branched chain nonylphenol, mixture of isomers (commercially available and which did not contain any n-nonylphenol) was almost as active as n-nonylphenol.

Nonylphenol ethoxylate and octylphenol ethoxylate are widely used as nonionic surfactants. Concern over the environmental and health impact of these alkoxylated alkylphenols has led to governmental restriction on the use of these surfactants in Europe, as well as voluntary industrial restrictions in the United States. Many industries have attempted to replace these preferred alkoxylated alkylphenol surfactants with alkoxylated linear and branched alkyl primary and secondary alcohols, but have encountered problems with odor, performance, formulating, and increased costs. Although the predominate focus has been on the alkylphenol ethoxylates and the potential problems associated with these compounds (primarily with the degradation by-products), there remains a need to review other components to select combinations that have similar or improved performance benefits with reduced negative impacts.

Nonylphenol and dodecylphenol can be produced by the following steps: propylene oligomerization and separation of propylene trimer and tetramer, and phenol alkylation with propylene trimer and separation of nonylphenol, or phenol alkylation with propylene tetramer and separation of dodecylphenol. Tetrapropenyl phenol prepared from propylene tetramer has been widely used in the lubricant additive industry. Propylene tetramer comprises carbon chains with a high degree of methyl branching and an average carbon number of 12. Generally the tetramer can have a carbon number distribution between 10 to 15 carbons. The tetramer imparts oil solubility and compatibility with other oil soluble lubricant additive components. A tetramer is also a cost effective olefin to manufacture. Dodecylphenol derived from propylene tetramer is primarily used as an intermediate in the production of additives for lubricating oils, commonly sulfurized alkyl phenate detergents. To a lesser degree, these branched phenate detergents have employed some degree of linear olefin.

U.S. Patent Application Publication No. 20070049508 ("the '508 application") discloses a lubricating oil composition containing (a) an oil of lubricating viscosity, and (b) a detergent containing an unsulfurized alkali or alkaline earth metal salt of a reaction product of (i) an olefin having at least 10 carbon atoms, wherein greater than 80 mole % of the olefin is a linear $C_{20}$ to $C_{30}$ n-alpha olefin, wherein less than 10 mole % of the olefin is a linear olefin of less than 20 carbon atoms, and wherein less than 5 mole % of the olefin is branched chain olefin of 18 carbons or less, and (2) a hydroxyaromatic compound. Comparative Example C in the '508 application discloses a branched pentadecylphenol calcium salt prepared by alkylating a phenol with a branched chain $C_{14}$ to $C_{18}$ olefin derived primarily from propylene pentamer. However, the '508 application discloses that the branched pentadecylphenol calcium salt of Comparative Example C was ineffective in preventing endocrine disruption effects. Furthermore, the '508 application does not disclose a boiling point range for the olefin.

U.S. Pat. No. 5,510,043 ("the '043 patent") discloses a lubricating oil additive containing (a) an alkaline earth metal salt of a sulfurized monoalkylcatechol derivative and (b) a sulfurized monoalkylcatechol. The '043 patent further discloses that the sulfurized monoalkylcatechol can be obtained by sulfurizing an alkylation product of a catechol produced by reacting a catechol with an olefin such as a propylene pentamer in the presence of a catalyst. There is no disclosure in the '043 patent of endocrine disruption effects. There is likewise no disclosure in the '043 patent of a boiling point range for the olefin used in the alkylcatechol synthesis.

It is desirable to develop improved lubricating oil additives derived from alkylphenols for use in lubricating oil compositions.

SUMMARY OF THE INVENTION

In accordance with one embodiment of the present invention, there is provided an overbased salt of an oligomerized alkylhydroxyaromatic compound, wherein the alkyl group of the alkylhydroxyaromatic compound is derived from an olefin mixture comprising propylene oligomers having an initial boiling point of at least about 195° C. and a final boiling point of greater than 325° C. and up to about 400° C. as measured by ASTM D86.

In accordance with a second embodiment of the present invention, there is provided a process for preparing an overbased salt of an oligomerized alkylhydroxyaromatic compound, the process comprising the steps of:
(a) alkylating a hydroxyaromatic compound with an olefin mixture comprising propylene oligomers having an initial boiling point of at least about 195° C. and a final boiling point of greater than 325° C. and up to about 400° C. as measured by ASTM D86, to provide an alkylhydroxyaromatic compound;
(b) neutralizing the alkylhydroxyaromatic compound of step (a) to provide a salt of the alkylhydroxyaromatic compound;
(c) oligomerizing the salt of the alkylhydroxyaromatic compound of step (b) to provide a salt of an oligomerized alkylhydroxyaromatic compound; and
(d) overbasing the salt of the oligomerized alkylhydroxyaromatic compound of step (c) to provide the overbased salt of the oligomerized alkylhydroxyaromatic compound.

In accordance with a third embodiment of the present invention, a lubricating oil composition is provided which comprises (a) a major amount of an oil of lubricating viscosity; and (b) an overbased salt of an oligomerized alkylhydroxyaromatic compound, wherein the alkyl group of the alkylhydroxyaromatic compound is derived from an olefin mixture comprising propylene oligomers having an initial boiling point of at least about 195° C. and a final boiling point of greater than 325° C. and up to about 400° C. as measured by ASTM D86.

In accordance with a fourth embodiment of the present invention, there is provided a method for reducing the endocrine disrupting properties of a lubricating oil composition on exposure to mammals, the method comprising adding an overbased salt of an oligomerized alkylhydroxyaromatic compound, wherein the alkyl group of the alkylhydroxyaromatic compound is derived from an olefin mixture comprising propylene oligomers having an initial boiling point of at least about 195° C. and a final boiling point of greater than 325° C. and up to about 400° C. as measured by ASTM D86, to a lubricating oil composition comprising a major amount of an oil of lubricating viscosity.

In accordance with a fifth embodiment of the present invention, the use of an overbased salt of an oligomerized alkylhydroxyaromatic compound, wherein the alkyl group of the alkylhydroxyaromatic compound is derived from an olefin mixture comprising propylene oligomers having an initial boiling point of at least about 195° C. and a final boiling point of greater than 325° C. and up to about 400° C. as measured by ASTM D86, as an additive in a lubricating oil composition comprising a major amount of an oil of lubricating viscosity, for the purpose of reducing the endocrine disrupting properties of the lubricating oil composition on exposure to mammals, is provided.

In accordance with a sixth embodiment of the present invention, the use of an overbased salt of an oligomerized alkylhydroxyaromatic compound, wherein the alkyl group of the alkylhydroxyaromatic compound is derived from an olefin mixture comprising propylene pentamers having an initial boiling point of at least about 195° C. and a final boiling point of greater than 325° C. and up to about 400° C. as measured by ASTM D86, as an additive in a lubricating oil composition comprising a major amount of an oil of lubricating viscosity, for the purpose of reducing the endocrine disrupting properties of the lubricating oil composition on exposure to mammals, is provided.

In accordance with a seventh embodiment of the present invention, there is provided a propylene oligomer having an initial boiling point of at least about 195° C. and a final boiling point of greater than 325° C. and up to about 400° C. as measured by ASTM D86, wherein the propylene oligomer contains a distribution of carbon atoms that comprise at least about 50 weight percent of $C_{14}$ to $C_{20}$ carbon atoms.

In accordance with an eighth embodiment of the present invention, there is provided a process comprising (a) contacting a feedstock comprising at least about 50 wt. % propylene, based on the total weight of the feedstock, with a liquid phosphoric acid catalyst having an acid strength of at least about 114% and up to about 122% in a reaction zone under oligomerization conditions; and (b) isolating a propylene oligomer having an initial boiling point of at least about 195° C. and a final boiling point of greater than 325° C. and up to about 400° C. as measured by ASTM D86, wherein the propylene oligomer contains a distribution of carbon atoms that comprise at least about 50 weight percent of $C_{14}$ to $C_{20}$ carbon atoms.

The endocrine disruption effects of lubricating oil additives derived from alkyl phenols are believed to be minimized by the use of the propylene oligomers of the present invention. Thus, propylene oligomers having an initial boiling point of at least about 195° C. and a final boiling point greater than 325° C. and up to about 400° C. are believed to minimize any potential endocrine disruption effects. The overbased salt of the oligomerized alkylhydroxyaromatic compound of the present invention is therefore believed to also be substantially free of endocrine disruptive chemicals. Accordingly, the overbased salt of the oligomerized alkylhydroxyaromatic compound of the present invention can advantageously be employed in compositions which require minimized endocrine disruption effects when exposed to mammals.

DETAILED DESCRIPTION OF THE PREFERRED EMBODIMENTS

The present invention is directed to an overbased salt of an oligomerized alkylhydroxyaromatic compound, wherein the alkyl group of the alkylhydroxyaromatic compound is derived from an olefin mixture comprising propylene oligomers having an initial boiling point of at least about 195° C. and a final boiling point of greater than 325° C. and up to about 400° C. as measured by ASTM D86.

Prior to discussing the invention in further detail, the following terms will be defined:

Definitions

As used herein, the following terms have the following meanings, unless expressly stated to the contrary:

The term "endocrine disrupter" as used herein is a compound which disrupts normal regulation of the endocrine system; in particular, the endocrine system that regulates reproductive processes.

The term "lime" as used herein refers to calcium hydroxide, also known as slaked lime or hydrated lime.

The term "Total Base Number" or "TBN" as used herein refers to the amount of base equivalent to milligrams of KOH in 1 gram of sample. Thus, higher TBN numbers reflect more alkaline products, and therefore a greater alkalinity reserve. The TBN of a sample can be determined by ASTM Test No. D2896 or any other equivalent procedure.

The overbased salt of an oligomerized alkylhydroxyaromatic compound of the present invention can be obtained by (a) alkylating a hydroxyaromatic compound with an olefin mixture comprising propylene oligomers having an initial boiling point of at least about 195° C. and a final boiling point greater than 325° C. and up to about 400° C. as measured by ASTM D86, to provide an alkylhydroxyaromatic compound; (b) neutralizing the alkylhydroxyaromatic compound of step (a) to provide a salt of the alkylhydroxyaromatic compound; (c) oligomerizing the salt of the alkylhydroxyaromatic compound of step (b) to provide a salt of an oligomerized alkylhydroxyaromatic compound; and (d) overbasing the salt of the oligomerized alkylhydroxyaromatic compound of step (c) to provide the overbased salt of the oligomerized alkylhydroxyaromatic compound.

In general, processes for preparing overbased salts of an oligomerized alkylhydroxyaromatic compound are well known and any known process for making overbased oligomerized alkylhydroxyaromatic salts may be employed herein. For example, representative processes for preparing such salts include U.S. Pat. Nos. 3,178,368 and 3,801,507 which disclose overbased sulfurized alkylphenates, U.S. Pat. No. 3,429,812 which discloses overbased alkylphenol/formaldehyde/diaminoalkane condensation products, and U.S. Pat. Nos. 5,281,346 and 5,458,793 which disclose neutralized alkylphenol-glyoxylic acid oligomers that may also be overbased. Accordingly, the steps employed in the process for making the overbased salt of an oligomerized alkylhydroxyaromatic compound of the present invention are within the purview of one skilled in the art.

In step (a), a hydroxyaromatic compound is alkylated with an olefin mixture containing at least the propylene oligomers. Useful hydroxyaromatic compounds which may be alkylated include mononuclear monohydroxy and polyhydroxy $C_6$ to $C_{30}$ aromatic hydrocarbons having 1 to 4 hydroxy groups, and in one embodiment 1 to 3 hydroxy groups. Suitable hydroxyaromatic compounds include phenol, catechol, resorcinol, hydroquinone, pyrogallol, cresol, and the like and mixtures thereof In one embodiment, a hydroxyaromatic compound is a phenol.

The olefin mixture for alkylating the hydroxyaromatic compound contains at least propylene oligomers having an initial boiling point of at least about 195° C. and a final boiling point greater than 325° C. and up to about 400° C. as measured by ASTM D86. In one embodiment, the propylene oligomers have an initial boiling point of at least about 220° C. as measured by ASTM D86. In one embodiment, the propylene oligomers have an initial boiling point of at least about 225° C. as measured by ASTM D86. In another embodiment, the propylene oligomers have an initial boiling point of at least about 235° C. as measured by ASTM D86. In yet another embodiment, the propylene oligomers have an initial boiling point of at least about 245° C. as measured by ASTM D86. In still yet another embodiment, the propylene oligomers have an initial boiling point of at least about 260° C. as measured by ASTM D86. In still another embodiment, the propylene oligomers have an initial boiling point of at least about 280° C. as measured by ASTM D86. In another embodiment, the propylene oligomers have an initial boiling point of at least about 300° C. as measured by ASTM D86.

In one embodiment, the propylene oligomers have a final boiling point of about 330° C. and up to about 400° C. as measured by ASTM D86. In another embodiment, the propylene oligomers have a final boiling point of about 335° C. and up to about 400° C. In yet another embodiment, the propylene oligomers have a final boiling point of about 330° C. to about 375° C. In a further embodiment, the propylene oligomers have a final boiling point of about 335° C. to about 360° C. Any combination of the foregoing initial boiling points and final boiling points for the propylene oligomers are contemplated herein.

The propylene oligomer can be obtained by contacting a feedstock comprising a major amount of propylene with a liquid phosphoric acid catalyst having an acid strength of at least about 114% and up to about 122% in a reaction zone under oligomerization conditions and isolating a propylene oligomer having an initial boiling point of at least about 195° C. and a final boiling point of greater than 325° C. and up to about 400° C. as measured by ASTM D86.

The feedstock for use in preparing the propylene oligomers will contain propylene in an amount of at least about 50 wt. %, based on the total weight of the feedstock. In one embodiment, the feedstock will contain propylene in an amount of at least about 60 wt. %, based on the total weight of the feedstock. In another embodiment, the feedstock will contain propylene in an amount of at least about 70 wt. %, based on the total weight of the feedstock. In one embodiment, the feedstock will contain propylene in an amount of at least about 80 wt. %, based on the total weight of the feedstock. In yet another embodiment, the feedstock will contain propylene in an amount of about 75 to about 90 wt. %, based on the total weight of the feedstock.

In one embodiment, the feedstock can contain relatively low amounts, if any (i.e., substantially free), of any olefin other than propylene, e.g., butene. In one embodiment, the feedstock can contain other olefins such as butene, provided that the oligomerization product of the reaction has an initial boiling point of greater than about 195° C. and a final boiling point of greater than 325° C. and up to about 400° C. In one embodiment, the feedstock contains less than about 10 wt. % butene. In another embodiment, the feedstock contains less than about 5 wt. % butane. In yet another embodiment, the feedstock contains less than about 2 wt. % butene. The feedstock can also contain relatively low amounts, typically less than about 10 wt. %, of non-reactive components such as alkanes, e.g., ethane, propane, butane, isobutane and the like.

In the process of the present invention, the conversion rate of the starting olefin (weight percent oligomerized product/total weight of starting olefin) is at least about 70 wt. %. In one embodiment, the conversion rate of the starting olefin is at least about 75 wt. %. In another embodiment, the conversion rate of the starting olefin is at least about 80 wt. %. In another embodiment, the conversion rate of the starting olefin is at least 85 wt. %.

In general, the liquid phosphoric acid catalyst for use in the process for preparing the propylene oligomers are known in the art, see, e.g., the liquid phosphoric acid-catalyst disclosed in, for example, U.S. Pat. Nos. 2,592,428, 2,814,655 and 3,887,634. The phosphoric acid catalyst strength can vary, but must be sufficient to produce a propylene oligomer with an initial boiling point of at least about 195° C. and a final boiling point of greater than 325° C. and up to about 400° C. as measured by ASTM D86. Useful liquid phosphoric acid catalysts for use herein have an acid strength of at least about 114% and up to about 122%. In one embodiment, useful liquid phosphoric acid catalysts have an acid strength of at least about 114% and up to about 118%. In one embodiment, useful liquid phosphoric acid catalysts have an acid strength of at least about 114% and up to about 116%. The strength of the phosphoric acid catalyst can be calculated by measuring the polyphosphoric acid peaks using NMR (nuclear magnetic resonance spectroscopy), and can be expressed as a percentage of $P_2O_5$ greater than that required for the hydrolysis reaction to make orthophosphoric acid ($H_3PO_4$). Orthophosphoric acid will have a strength of 100%, pyrophosphoric acid ($H_4P_2O_7$) will have a strength of 110%, and polyphosphoric acid $H_4P_2O_7(HPO_3)_n$, will have a strength of 114% when n=1 and a strength of 116% when n=2.

The feedstock and liquid phosphoric acid catalyst are contacted in a reaction zone at a temperature and at a pressure sufficient to maintain the normally gaseous feedstock in a liquid state. In general, the feedstock and liquid phosphoric acid catalyst can be contacted while maintaining the temperature of the reaction zone at about 75° C. to about 175° C., with a pressure of from about 200 psig to about 1600 psig. In one embodiment, the temperature can range from about 85° C. to about 150° C. In another embodiment, the temperature can range from 100° C. to about 150° C. In one embodiment, the temperature can range from about 110° C. to about 125° C. In one embodiment, the pressure in the reaction zone can range from about 400 psig to about 1000 psig. In another embodiment, the pressure can range from about 500 psig to about 850 psig. In another embodiment, the pressure can range from 550 psig to about 800 psig. Any combination of the foregoing temperature and pressure ranges are contemplated herein.

Generally, the feedstock and liquid phosphoric acid catalyst are contacted for a time period ranging from about 5 minutes to about 45 minutes.

Once the feedstock and liquid phosphoric acid catalyst have been contacted in the reaction zone under oligomerization conditions, a propylene oligomer having an initial boiling point of at least about 195° C. and a final boiling point of greater than 325° C. and up to about 400° C. as measured by ASTM D86, wherein the propylene oligomer contains a distribution of carbon atoms that comprise at least about 50 weight percent of $C_{14}$ to $C_{20}$ carbon atoms is isolated by techniques known in the art, e.g., by distillation.

In one embodiment, a propylene oligomer employed herein can contain a distribution of carbon atoms that comprise no more than about 25 wt. % of $C_{14}$ or lower carbon atoms. In one embodiment, a propylene oligomer employed herein can contain a distribution of carbon atoms that comprise no more than about 20 wt. % of $C_{14}$ or lower carbon atoms. In another embodiment, a propylene oligomer employed herein can contain a distribution of carbon atoms that comprise no more than about 15 wt. % of $C_{14}$ or lower carbon atoms. In one embodiment, a propylene oligomer employed herein can contain a distribution of carbon atoms that comprise no more than about 5 wt. % of $C_{14}$ or lower carbon atoms.

In one embodiment, a propylene oligomer employed herein can contain a distribution of carbon atoms that comprise less than about 3% of $C_{13}$ and lower carbon atoms. In one embodiment, a propylene oligomer employed herein can contain a distribution of carbon atoms that comprise less than about 2% of $C_{13}$ and lower carbon atoms. In one embodiment, a propylene oligomer employed herein can contain a distribution of carbon atoms that comprise less than about 1% of $C_{13}$ and lower carbon atoms. In one embodiment, a propylene oligomer employed herein is substantially free of any $C_{13}$ and lower carbon atoms.

In one embodiment, a propylene oligomer employed herein can contain a distribution of carbon atoms that comprise at least about 50 wt. % of $C_{14}$ to $C_{20}$ carbon atoms. In another embodiment, a propylene oligomer employed herein can contain a distribution of carbon atoms that comprise at least about 55 wt. % $C_{15}$ to $C_{20}$ carbon atoms.

In one embodiment, a propylene oligomer employed herein can contain a distribution of carbon atoms that comprise at least about 10 wt. % $C_{21}$ to $C_{26}$ carbon atoms. In another embodiment, a propylene oligomer employed herein can contain a distribution of carbon atoms that comprise at least about 1 wt. % of $C_{27+}$ carbon atoms. In another embodiment, a propylene oligomer employed herein can contain a distribution of carbon atoms that comprise at least about 1 wt. % $C_{27+}$ carbon atoms and up to about 5 wt. % $C_{27+}$ carbon atoms.

In another embodiment, a propylene oligomer employed herein can contain a distribution of carbon atoms that comprise at least about at least 50 wt. % $C_{14}$ to $C_{20}$, at least about 10 wt. % $C_{21}$ to $C_{26}$, and at least about 1 wt.% $C_{27+}$ carbon atoms. In another embodiment, a propylene oligomer employed herein can contain a distribution of carbon atoms that comprise at least about 55 wt. % $C_{14}$ to $C_{20}$, at least about 10 wt. % $C_{21}$ to $C_{26}$, and at least about 1 wt. % $C_{27+}$ carbon atoms.

Any combination of the foregoing distribution of carbon atoms for the propylene oligomers are contemplated herein.

The propylene oligomers of the present invention may comprise any amount of low molecular weight propylene oligomer such as propylene trimer or tetramer as long as the initial boiling point of the mixture of propylene oligomers is at least about 195° C. The propylene oligomers of the present invention may also contain any amount of high molecular weight propylene oligomer such as $C_{27+}$, provided that the final boiling point is greater than 325° C. and up to about 400° C. as measured by ASTM D86. In one embodiment, the propylene oligomers of the present invention can contain tetramers, pentamers, hexamers, heptamers, octamers, nonamers, and mixtures thereof.

Generally, the olefin mixture will contain a major mount of the foregoing propylene oligomers. However, as one skilled in the art will readily appreciate, the olefin mixture can contain other olefins. For example, the other olefins that can be used in the olefin mixture include linear olefins, cyclic olefins, branched olefins other than propylene oligomers such as butylene or isobutylene oligomers, arylalkylenes and the like and mixtures thereof. Suitable linear olefins include 1-hexene, 1-nonene, 1-decene, 1-dodecene and the like and mixtures thereof. Especially suitable linear olefins are high molecular weight normal alpha-olefins such as $C_{16}$ to $C_{30}$ normal alpha-olefins, which can be obtained from processes such as ethylene oligomerization or wax cracking. Suitable cyclic olefins include cyclohexene, cyclopentene, cyclooctene and the like and mixtures thereof. Suitable branched olefins include butylene dimer or trimer or higher molecular weight isobutylene oligomers, and the like and mixtures thereof. Suitable arylalkylenes include styrene, methyl styrene, 3-phenylpropene, 2-phenyl-2-butene and the like and mixtures thereof.

Alkylation of the hydroxyaromatic compound with the olefin mixture is generally carried out in the presence of an alkylation catalyst. Useful alkylation catalysts include Lewis acids, solid acids, trifluoromethanesulfonic acid, and acidic molecular sieve catalysts. Suitable Lewis acids include aluminum trichloride, boron trifluoride and boron trifluoride complexes, such as boron trifluoride etherate, boron trifluoride-phenol and boron trifluoride-phosphoric acid. Suitable solid acids include the sulfonated acidic ion exchange resin type catalysts include Amberlyst 36®, available from Rohm and Haas (Philadelphia, Pa.).

The reaction conditions for the alkylation depend upon the type of catalyst used, and any suitable set of reaction conditions that result in high conversion to the alkylhydroxyaromatic product without unacceptable amounts of cracking can be employed. In one preferred embodiment of the present invention, the alkylhydroxyaromatic compound that is the product of alkylation contains no more than about 10%, preferably no more than about 5%, more preferably no more than 2%, and most preferably no more than 1% of alkylhydroxyaromatic in which the alkyl group is $C_{13}$ or less. In another embodiment, the alkylhydroxyaromatic compound that is the product of alkylation contains at least about 20%, preferably at least about 30%, more preferably at least about 40%, and most preferably at least about 50% of alkylhydroxyaromatic in which the alkyl group is $C_{15}$ to $C_{20}$.

In one embodiment, the reaction temperature for the alkylation reaction will be in the range of about 25° C. to about 200° C. In another embodiment, the reaction temperature for the alkylation reaction will be in the range of about 85° C. to about 135° C. The reaction pressure will generally be atmospheric, although higher or lower pressures may be employed. The alkylation process can be practiced in a batchwise, continuous or semi-continuous manner. In one embodiment, the molar ratio of the hydroxyaromatic compound to olefin mixture is normally in the range of about 10:1 to about 0.5:1. In one embodiment, the molar ratio of the hydroxyaromatic compound to olefin mixture is normally in the range of about 5:1 to about 3:1.

The alkylation reaction may be carried out neat or in the presence of a solvent which is inert to the reaction of the hydroxyaromatic compound and the olefin mixture. When employed, a typical solvent is hexane.

Upon completion of the reaction, the desired alkylhydroxyaromatic compound can be isolated using conventional techniques. Typically, excess hydroxyaromatic compound is distilled from the reaction product.

The alkyl group of the alkylhydroxyaromatic compound is typically attached to the hydroxyaromatic compound primarily in the ortho and para positions.

The alkylhydroxyaromatic compound thus obtained can then be contacted with a metal base under reactive conditions, preferably in an inert-compatible liquid hydrocarbon diluent to provide a salt of the alkylhydroxyaromatic compound. Preferably, the reaction is conducted under an inert gas, typically nitrogen. The metal base may be added either in a single addition or in a plurality of additions at intermediate points during the reaction.

Suitable metal basic compounds include hydroxides, oxides or alkoxides of the metal such as (1) an alkali or alkaline earth metal salt derived from a metal base selected from an alkali hydroxide, alkali oxide or an alkali alkoxide, or (2) an alkaline earth metal salt derived from a metal base selected from an alkaline earth hydroxide, alkaline earth oxide or alkaline earth alkoxide. Representative examples of metal basic compounds with hydroxide functionality include lithium hydroxide, potassium hydroxide, sodium hydroxide, magnesium hydroxide, calcium hydroxide, barium hydroxide and aluminum hydroxide. Representative examples of metal basic compounds with oxide functionality include lithium oxide, magnesium oxide, calcium oxide and barium oxide. Preferably, the metal base used is calcium hydroxide because of its handling convenience and cost versus, for example, calcium oxide.

The neutralization reaction between the metal base and the alkylhydroxyaromatic compound is typically conducted at temperatures above room temperature (25° C.). The neutralization reaction is carried out in the presence of a promoter such as ethylene glycol, formic acid, acetic acid, and the like and mixtures thereof.

The salt of the alkylhydroxyaromatic compound is then oligomerized to provide a salt of an oligomerized alkylhydroxyaromatic compound. In theory, neutralization can be conducted as a separate step prior to oligomerization, but neutralization and oligomerization can be carried out together in a single process step. Where the neutralization is conducted as a separate step, both the neutralization and the subsequent oligomerization step are conducted under the same conditions as set forth above.

In one embodiment, oligomerization can be carried out by contacting the salt of the alkylhydroxyaromatic compound with a sulfur source optionally in the presence of an oligomerization promoter. Any suitable sulfur source can be used for the oligomerization step such as, for example, elemental sulfur, hydrogen sulfide, sulfur dioxide and sodium sulfide hydrates. The sulfur can be employed either as molten sulfur or as a solid (e.g., powder or particulate) or as a solid suspension in a compatible hydrocarbon liquid. A suitable oligomerization promoter is a polyol, typically an alkylene diol, e.g., ethylene glycol. Based on one mole of the salt of the alkylhydroxyaromatic compound, typically about 0.5 to about 4, and preferably from about 2 to about 3 moles of sulfur are used.

In conjunction with the promoter or mixture of promoters above, a high molecular weight alkanol can be employed as a co-solvent. These high molecular weight alkanols have straight or branched chain alkyls containing 8 to about 16 carbon atoms, and preferably 9 to about 15 carbon atoms. Representative examples of suitable alkanols include 1-octanol, 1-decanol (decyl alcohol), 2-ethyl-hexanol, and the like. Particularly preferred is 2-ethyl-hexanol. It is beneficial to use a high molecular weight alkanol in the process because it acts as a solvent and also forms an azeotrope with water and hence affords a convenient way to remove the water generated by the neutralization or any other water in the system, by azeotropic distillation either after or preferably during the reaction. The high molecular weight alkanol may also play some part in the chemical reaction mechanism in the sense that it facilitates the removal of the byproduct water during the reaction, thus pushing the reaction to the right of the reaction equation.

In another embodiment, oligomerization can be carried out by contacting the salt of the alkylhydroxyaromatic compound with an aldehyde to form, e.g., a salt of a methylene-bridged alkylhydroxyaromatic compound. Suitable aldehydes include aliphatic aldehydes, aromatic aldehydes, heterocyclic aldehydes and the like and mixtures thereof Representative examples of such aldehydes include formaldehyde, glyoxylic acid, acetaldehyde, propionaldehyde, butyraldehyde, glycoxal, furaldehyde 2-methyl-propionaldehyde, 2-methyl-butyraldehyde, 3-methyl-butyraldehyde, 2,3-dimethyl-butyraldehyde, 3,3-dimethyl-butyraldehyde, pentanal, methyl substituted pentanal, benzaldehyde, furfural and the like and mixtures thereof. The aldehyde may contain a substituent group such as a hydroxyl, halogen, nitrogen and the like so long as the substituent does not take a major part in the reaction. Preferably, the aldehyde is glyoxylic acid or a formaldehyde component. Formaldehyde is available in many forms for example as a solid, liquid or gas. Particularly preferred is paraformaldehyde (which is a solid typically a powder or flaked product containing the equivalent of about 91% to about 93% formaldehyde). Trioxane a crystalline solid may be employed (trioxane is the cyclic trimer of formaldehyde). However, liquid formaldehyde solutions may also be employed such as formalin solutions (aqueous solutions of formaldehyde, sometimes in methanol, in 37%, 44%, or 50% formaldehyde concentrations are commonly used forms) or formaldehyde in an aqueous solution. Additionally, formaldehyde is also available as a gas.

In another embodiment, oligomerization can be carried out by contacting the salt of the alkylhydroxyaromatic compound with an aldehyde and an amine source in a well-known Mannich reaction. Suitable aldehydes include any of the aldehydes discussed hereinabove. In one embodiment, the amine source contemplated herein is an amine which contains an amino group characterized by the presence of at least one active hydrogen atom. Such amines may contain only primary amino groups, only secondary amino groups, or both primary and secondary groups. The amine may be a mono or polyamine. Representative examples of useful amine compounds include N-methylamine, N-ethylamine, N-n-propylamine, N-isopropylamine, N-n-butylamine, N-isobutylamine, N-sec-butylamine, N-tert-butylamine, N-n-pentylamine, N-cyclopentylamine, N-n-hexylamine, N-cyclohexylamine, N-octylamine, N-decylamine, N-dodecylamine, N-octadecylamine, N-benzylamine, N-(2-phenylethyl)amine, 2-aminoethanol, 3-amino-1-proponal, 2-(2-aminoethyoxy)ethanol, N-(2-methoxyethyl)amine, N-(2-ethoxyethyl)amine, N,N-dimethylamine, N,N-diethylamine, N,N-di-n-propylamine, N,N-diisopropylamine, N,N-di-n-butylamine, N,N-di-sec-butylamine, N,N-di-n-pentylamine, N,N-di-n-hexylamine, N,N-dicyclohexylamine, N,N-dioctylamine, N-ethyl-N-methylamine, N-methyl-N-n-propylamine, N-n-butyl-N-methylamine, N-methyl-N-octylamine, N-ethyl-N-isopropylamine, N-ethyl-N-octylamine, N,N-di (2-hydroxyethyl)amine, N,N-di(3-hydroxypropyl)amine, N,N-di(ethoxyethyl)amine, N,N-di(propoxyethyl)amine, ethylene diamine, diethylene triamine, triethylene tetraamine, tetraethylene pentamine, and pentaethylene hexamine, o-, m- and p-phenylene diamine, diamino naphthalenes, N-acetyl tetraethylenepentamine, and the corresponding formyl-, propionyl-, butyryl-, and the like N-substituted compounds, morpholine, thiomorpholine, pyrrole, pyrroline, pyrrolidine, indole, pyrazole, pyrazoline, pyrazolidine, imidazole, imidazoline, imidazolidine, piperidine, phenoxazine, phenthiazine and their substituted analogs, and the like.

In a second embodiment, the amine source is an amino acid or salt thereof. By "amino acid" is meant any organic acid containing at least one primary, secondary or tertiary amine (—N<) group and at least one acidic carboxyl (—COOH) group. Mixtures of different amino acids can be used. Representative examples of amino acids include glycine, alanine, beta-alanine, valine, leucine, isoleucine, phenylalanine, serine, threonine, tyrosine, methionine, 6-aminohexanoic acid, proline, hydroxyproline, tryptophan, histidine, lysine, hydroxylysine, arginine, aspartic acid, asparagine, glutamic acid, glutamine, cysteine, cystine, ethylenediaminetetraacetic acid and nitrilotriacetic acid and other alpha-amino acids containing 1 to 5 carboxyl groups. Particularly preferred are the amino acids which are readily available in commercial quantities such as glycine, β-alanine, nitrilotriacetic acid, etc.

Typical Mannich reactions are well known in the art, for example, as disclosed in U.S. Pat. Nos. 3,368,972, 3,649,229; 4,157,309 and 5,370,805, the contents of which are incorporated by reference herein.

The resulting salt of an oligomerized alkylhydroxyaromatic compound is then overbased by reaction with an acidic overbasing compound, such as carbon dioxide or boric acid. A particularly preferred overbasing process is carbonation, i.e., a reaction with carbon dioxide. Such carbonation can be conveniently effected by addition of a polyol, typically an alkylene diol, e.g., ethylene glycol, and carbon dioxide to the salt of an oligomerized alkylhydroxyaromatic compound. Conveniently, the reaction is conducted by the simple expedient of bubbling gaseous carbon dioxide through the reaction mixture. Excess diluent and any water formed during the overbasing reaction can be conveniently removed by distillation either during or after the reaction.

Another embodiment of the present invention is directed to a lubricating oil composition containing at least (a) a major amount of an oil of lubricating viscosity; and (b) an overbased salt of an oligomerized alkylhydroxyaromatic compound of this invention which is useful as a lubricating oil additive. The lubricating oil compositions can be prepared by admixing, by conventional techniques, an appropriate amount of the lubricating oil additive of this invention with a base oil of lubricating viscosity. The selection of the particular base oil depends on the contemplated application of the lubricant and the presence of other additives. Generally, the overbased salt of an oligomerized alkylhydroxyaromatic compound of this invention will be present in the lubricating oil compositions in an amount of about 0.01 to about 40 wt. % and preferably from about 0.1 to about 20 wt. %, based on the total weight of the lubricating oil composition.

The oil of lubricating viscosity for use in the lubricating oil compositions of this invention, also referred to as a base oil, is typically present in a major amount, e.g., an amount of greater than 50 wt. %, preferably greater than about 70 wt. %, more preferably from about 80 to about 99.5 wt. % and most preferably from about 85 to about 98 wt. %, based on the total weight of the composition. The expression "base oil" as used herein shall be understood to mean a base stock or blend of base stocks which is a lubricant component that is produced by a single manufacturer to the same specifications (independent of feed source or manufacturer's location); that meets the same manufacturer's specification; and that is identified by a unique formula, product identification number, or both. The base oil for use herein can be any presently known or later-discovered oil of lubricating viscosity used in formulating lubricating oil compositions for any and all such applications, e.g., engine oils, marine cylinder oils, functional fluids such as hydraulic oils, gear oils, transmission fluids, etc. Additionally, the base oils for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (C). Generally, individually the base oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fischer-Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500-1000, diethyl ether of polypropylene glycol having a molecular weight of 1,000-1,500, etc.) or mono- and polycarboxylic esters thereof such as, for example, the acetic esters, mixed $C_3$-$C_8$ fatty acid esters, or the $C_{13}$ oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methyl-hexyl)silicate, tetra-(p-tertbutylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphonic acid, etc., polymeric tetrahydrofurans and the like.

The lubricating oil may be derived from unrefined, refined and rerefined oils, either natural, synthetic or mixtures of two or more of any of these of the type disclosed hereinabove.

Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The lubricating oil compositions of the present invention may also contain other conventional additives for imparting auxiliary functions to give a finished lubricating oil composition in which these additives are dispersed or dissolved. For example, the lubricating oil compositions can be blended with antioxidants, anti-wear agents, detergents such as metal detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and the like and mixtures thereof. A variety of the additives are known and commercially available. These additives, or their analogous compounds, can be employed for the preparation of the lubricating oil compositions of the invention by the usual blending procedures.

Examples of antioxidants include, but are not limited to, aminic types, e.g., diphenylamine, phenyl-alpha-napthylamine, N,N-di(alkylphenyl)amines; and alkylated phenylene-diamines; phenolics such as, for example, BHT, sterically hindered alkyl phenols such as 2,6-di-tert-butylphenol, 2,6-di-tert-butyl-p-cresol and 2,6-di-tert-butyl-4-(2-octyl-3-propanoic)phenol; and mixtures thereof.

Examples of ashless dispersants include, but are not limited to, polyalkylene succinic anhydrides; non-nitrogen containing derivatives of a polyalkylene succinic anhydride; a basic nitrogen compound selected from the group consisting of succinimides, carboxylic acid amides, hydrocarbyl monoamines, hydrocarbyl polyamines, Mannich bases, phosphonoamides, and phosphoramides; triazoles, e.g., alkyltriazoles and benzotriazoles; copolymers which contain a carboxylate ester with one or more additional polar function, including amine, amide, imine, imide, hydroxyl, carboxyl, and the like, e.g., products prepared by copolymerization of long chain alkyl acrylates or methacrylates with monomers of the above function; and the like and mixtures thereof. The derivatives of these dispersants, e.g., borated dispersants such as borated succinimides, may also be used.

Examples of rust inhibitors include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof.

Examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, preferably a $C_6$ to $C_{24}$, and most preferably a $C_6$ to $C_{20}$, fatty acid ester and a nitrogen-containing compound selected from the group consisting of ammonia, and an alkanolamine and the like and mixtures thereof.

Examples of antifoaming agents include, but are not limited to, polymers of alkyl methacrylate; polymers of dimethylsilicone and the like and mixtures thereof.

Each of the foregoing additives, when used, is used at a functionally effective amount to impart the desired properties to the lubricant. Thus, for example, if an additive is a friction modifier, a functionally effective amount of this friction modifier would be an amount sufficient to impart the desired friction modifying characteristics to the lubricant. Generally, the concentration of each of these additives, when used, ranges from about 0.001% to about 20% by weight, and in one embodiment about 0.01% to about 10% by weight based on the total weight of the lubricating oil composition.

The final application of the lubricating oil compositions of this invention may be, for example, in marine cylinder lubricants in crosshead diesel engines, trunk piston engine oils, crankcase lubricants in automobiles and railroads and the like, functional fluids, lubricants for heavy machinery such as steel mills and the like, or as greases for bearings and the like. Whether the lubricating oil composition is fluid or solid will ordinarily depend on whether a thickening agent is present. Typical thickening agents include polyurea acetates, lithium stearate and the like.

In another aspect of the present invention, in addition to being alkylating agents to form an alkylhydroxyaromatic compound intermediate used to make the overbased salts of this invention, the propylene oligomers described herein can also be employed to form reaction products other than alkylhydroxyaromatic compounds. For example, the propylene oligomers described herein can also be employed to form oxo alcohols, alkylhydroxyaromatic alkoxylates such as alkylphenol ethoxylates, alkylaromatics such as alkylbenzenes and alkyltoluenes, alkylated diphenylamines, alkyl mercaptans and the like. Methods for forming these reaction products are within the purview of one skilled in the art. The propylene oligomers of the invention may also find use directly as, e.g., high boiling point organic solvents.

In another embodiment of the invention, the lubricating oil additive of the present invention may be provided as an additive package or concentrate in which the additive is incorporated into a substantially inert, normally liquid organic diluent such as, for example, mineral oil, naphtha, benzene, toluene or xylene to form an additive concentrate. These concentrates usually contain from about 20% to about 80% by weight of such diluent. Typically, a neutral oil having a viscosity of about 4 to about 8.5 cSt at 100° C. and preferably about 4 to about 6 cSt at 100° C. will be used as the diluent, though synthetic oils, as well as other organic liquids which are compatible with the additives and finished lubricating oil can also be used. The additive package will also typically contain one or more of the various other additives, referred to above, in the desired amounts and ratios to facilitate direct combination with the requisite amount of oil of lubricating viscosity.

The following non-limiting examples are illustrative of the present invention.

EXAMPLE 1

Preparation of a Propylene Oligomer.

A propylene oligomer was obtained from an oligomerization process that employed a propylene-rich feedstock (on average 81.4 wt. % propylene, 17.4 wt. % propane, 0.8 wt % ethane, and 0.4 wt. % isobutane) and a bulk liquid phosphoric acid catalyst. The feed rate was 7.1 KBPD (thousand barrels per day), the pressure was 670 psig, and the temperature was 245° F. (118° C.). The phosphoric acid catalyst had an acid strength of between 114% to 115% during the oligomerization reaction. The propylene oligomer was distilled as a bottoms fraction and had an initial boiling point of 248.5° C., a final boiling point of 342.9° C. as measured by ASTM D86 and the following carbon number distribution as set forth below in Table 1.

TABLE 1

| | Wt. % |
|---|---|
| $C_{13}$ | 0 |
| $C_{14}$ | 3.1 |
| $C_{15}$ | 21.3 |
| $C_{16}$ | 15.1 |
| $C_{17}$ | 12.8 |
| $C_{18}$ | 13.6 |
| $C_{19}$ | 7.3 |
| $C_{20}$ | 6.6 |
| $C_{21}$ | 7.1 |
| $C_{22}$ | 3.2 |
| $C_{23}$ | 2.8 |
| $C_{24}$ | 2.7 |
| $C_{25}$ | 1.5 |
| $C_{26}$ | 1.2 |
| $C_{27+}$ | 1.7 |

EXAMPLE 2-5

Preparation of Propylene Oligomers.

Propylene oligomers were made using the same components, amounts and conditions as in Example 1 with the propylene oligomers distilled at different time points during the oligomerization reaction. The initial boiling points, final boiling points, and carbon number distributions are set forth below in Table 2.

TABLE 2

| | Ex. 2 | Ex. 3 | Ex. 4 | Ex. 5 |
|---|---|---|---|---|
| IBP (° C.) | 221 | 228 | 229 | 249 |
| FBP (° C.) | 338 | 327 | 336 | 336 |

TABLE 2-continued

| | Ex. 2 | Ex. 3 | Ex. 4 | Ex. 5 |
|---|---|---|---|---|
| $C_{12-}$ | 0 | 0 | 0 | 0 |
| $C_{12}$ | 9.7 | 0.9 | 0.6 | 0.6 |
| $C_{13}$ | 0 | 4.4 | 6.4 | 6.4 |
| $C_{14}$ | 13.6 | 13.7 | 14.0 | 14.0 |
| $C_{15}$ | 19.5 | 20.7 | 20.6 | 20.6 |
| $C_{16}$ | 10.1 | 10.9 | 11.1 | 11.1 |
| $C_{17}$ | 9.4 | 10.3 | 9.7 | 9.7 |
| $C_{18}$ | 10.5 | 11.4 | 10.7 | 10.7 |
| $C_{19}$ | 5.5 | 6.0 | 5.6 | 5.6 |
| $C_{20}$ | 5.0 | 5.2 | 4.9 | 4.9 |
| $C_{21}$ | 5.2 | 5.2 | 5.3 | 5.3 |
| $C_{22}$ | 2.5 | 2.9 | 2.4 | 2.4 |
| $C_{23}$ | 2.2 | 2.2 | 2.2 | 2.2 |
| $C_{24}$ | 2.3 | 2.2 | 2.2 | 2.2 |
| $C_{25}$ | 1.2 | 1.3 | 1.3 | 1.3 |
| $C_{26}$ | 1.0 | 1.2 | 1.0 | 1.0 |
| $C_{27+}$ | 2.3 | 1.5 | 1.2 | 1.2 |

EXAMPLE 6

Preparation of an Alkylhydroxyaromatic Compound.

An alkylphenol was made by alkylating phenol with the propylene oligomer of Example 1. To a 4 liter round bottom flask was added 744 g (3.03 moles) of the propylene oligomer of Example 1 and 1128 g of phenol (12 moles). The reactants were mixed and heated to 80° C. At this temperature, 89.3 g of Amberlyst® 36 catalyst (Rohm and Haas) was added and the temperature of the reaction mixture was raised to 110° C. The reaction proceeded for 4 hours at this temperature under nitrogen at atmospheric pressure. The reaction mixture was cooled to 100° C. and filtered to remove the catalyst. Next, the reaction mixture was heated to 230° C. under 30 mm Hg vacuum and held under those conditions for 15 minutes in order to distill excess phenol. The obtained alkylphenol had the following analysis:
% monoalkylphenol: 92.85%
% para: 87.76%
% ortho: 5.09%
% dialkylphenol: 1.34%
% unreacted olefin: 4.39%
% ether: 1.29%
% phenol: 0.13%

EXAMPLE 7

Preparation of an Overbased Salt of an Oligomerized Alkylphenol.

802 g of the alkylated phenol from Example 6 was combined with 747 grams of 130N oil, 44.1 grams of an alkylaryl sulfonic acid, and 0.2 grams of foam inhibitor SI 200 available from Dow Corning and charged in a 4 liter flask at ambient temperature. The mixture was warmed over 25 minutes to 110° C., and while warming 380 grams of hydrated lime was added. After the warming phase and after lime addition was completed, 112.7 grams of sulfur were added and the reaction temperature was increased to 150° C. over 20 minutes. After the sulfur addition phase, the pressure of the reactor was reduced to 680 mmHg. $H_2S$ gas that was produced during the sulfurization was trapped by two caustic soda bubblers. At 150° C., 58.2 grams of ethylene glycol was added over 45 minutes. Over a 15 minute period, 328 grams of 2-ethylhexanol was added at 150° C. Then, the reaction was allowed to heat back up to 170° C. during one hour, at this step 95.5 grams of ethylene glycol was added.

Following the ethylene glycol addition, the pressure was slightly increased to 720 mmHg and reaction conditions were maintained for 20 minutes. Maintaining the temperature at 170° C., the pressure was increased to 760 mmHg. Once at atmospheric pressure, 9 grams of carbon dioxide were added over 30 minutes. After the addition of carbon dioxide, 79.2 grams of ethylene glycol were added over one hour and the rate of $CO_2$ was increased to 0.8 g/minute. This carbonation step was stopped when roughly 120 grams of $CO_2$ was added.

Over a one hour period, the solvent was distilled at 215° C. and 30 mmHg. The temperature was then further increased to 220° C. with a nitrogen purge at 80 mmHg over the course of an hour. The product was filtered with celite at 165° C. and the filtered overbased salt of the alkylphenol was degassed under air over four hours at 5 liter/hour/kg of product at 150° C. The product had 9.46% Ca; 3.2% S; a kinematic viscosity at 100° C. of 235.2 cSt.; and a TBN of 260 mg KOH/g.

Comparative Example 1

Preparation of a Propylene Tetramer

A propylene tetramer was prepared in essentially the same manner as the propylene oligomer in Example 1, with the exception of the phosphoric acid strength being between 111% to 112%. The resulting propylene tetramer had an initial boiling point of 180° C. and a final boiling point of 219° C. as measured by ASTM D86. The carbon distribution of the propylene tetramer is set forth below in Table 3.

TABLE 3

|  | Wt. % |
| --- | --- |
| $C_9$ | 2.1 |
| $C_{10}$ | 3.5 |
| $C_{11}$ | 6.3 |
| $C_{12}$ | 59.5 |
| $C_{13}$ | 8.2 |
| $C_{14}$ | 7.0 |
| $C_{15}$ | 12.0 |
| $C_{16+}$ | 1.3 |

Comparative Example 2

Preparation of an Alkylphenol

An alkylphenol was prepared in essentially the same manner as in Example 3, except that the propylene tetramer of Comparative Example 1 was used in place of the propylene oligomer of Example 1. The resulting alkylphenol had the following analysis:
% monoalkylphenol: 95.84%
para: 87.97%
% ortho: 7.87%
% dialkylphenol: 1.73%
% light alkylphenol: 1.54%
% unreacted olefin: 4.39%
% ether: 0.59%
% phenol: 1.03%

Comparative Example 3

Preparation of an Overbased Sulfurized Alkylphenol from a Propylene Tetramer Alkylphenol.

An overbased sulfurized alkylphenol was made using the alkylphenol described in Comparative Example 2 and following the essentially the same procedure as in Example 4. The resulting overbased sulfurized alkylphenol had the following analysis: 9.68% Ca; 3.37% S; a kinematic viscosity at 100° C. of 406.3 cSt; and a TBN of 271 mg KOH/g.

Comparative Example 4

Preparation of Additive Package

An additive package was prepared containing (a) 24.1 wt. % of the overbased sulfurized alkylphenol of Comparative Example 3; (b) 35.2 wt. % of an oil concentrate of a ethylene carbonate-treated bis-succinimide dispersant derived from 2300 MW polybutene; (c) 10.6 wt. % of an oil concentrate of a low overbased calcium sulfonate; (d) 13.4 wt. % of an oil concentrate of a secondary zinc dithiophosphate anti-wear agent; (e) 1.7 wt. % of an oil concentrate of a molybdenum oxysulfide complex of a succinimide dispersant derived from 1000 MW polybutene; (f) 3.11 wt. % of a borated glycerol mono-oleate friction modifier; (g) 0.05 wt. % of a foam inhibitor; and (h) the balance being Exxon 150N (a Group I base oil) commercially available from EXXONMOBIL Corporation.

Comparative Example 5

Preparation of Lubricating Oil Composition

A lubricating oil composition was prepared by adding the additive package of Comparative Example 4 to a mixture of 8.9 wt. % of a viscosity index improver (Paratone 8004) and 91.1 wt. % of a mixture of 74 wt. % of Exxon 150N Group I base oil and 26 wt. % of Exxon 600N (a Group I base oil) commercially available from EXXONMOBIL Corporation. The final concentration of the additive package in the lubricating oil composition was 9.65 wt. %.

EXAMPLE 8

Preparation of Additive Package

An additive package was prepared containing the same components and amounts as in Comparative Example 4 except that the overbased sulfurized alkylphenol of Comparative Example 3 was replaced with 23.6 wt. % of the overbased salt of the oligomerized alkylphenol of Example 7.

EXAMPLE 9

Preparation of Lubricating Oil Composition

A lubricating oil composition was prepared by adding the additive package of Example 8 to a mixture of 8.9 wt. % of a viscosity index improver (Paratone 8004) and 91.1 wt. % of a mixture of 74 wt. % of Exxon 150N Group I base oil and 26 wt. % of Exxon 600N Group I base oil. The final concentration of the additive package in the lubricating oil composition was 9.65 wt. %.

Testing

Compatibility Test 1

The additive package of Example 8 and the additive package of Comparative Example 4 were compared in Compatibility Test 1. This test evaluates the tendency of an additive package to form sediments, flocculation, or gel over time. The additive package was poured into a glass flask and stored at 20° C. To test the compatibility of the package at 80° C., packages were exposed to the following daily heating cycle: 80° C. for 8 hours and then 20° C. for 14 hours. The test was run for 28 days and evaluated at the end of this time period. The ratings were based on the following scale:

0=free of sediment
1=hazy but no sediment
2=sediment present
3=gelled

The results are set forth below in Table 4.

The lubricating oil compositions of Example 9 and Comparative Example 5 were also evaluated using Compatibility Test 1 under the same time and temperature conditions. The results are set forth below in Table 4.

Compatibility Test 2

In order to further demonstrate the compatibility of the overbased salts of an oligomerized alkylphenol of the invention, the compatibility of an additive package containing the overbased salt of an oligomerized alkylphenol of Example 7 and the overbased sulfurized alkylphenol of Comparative Example 3 were combined individually within an additive package containing a high overbased calcium sulfonate on an equal calcium basis; that is, each package contained 100 millimoles of calcium per kg of additive package from the overbased salt of an oligomerized alkylphenol of Example 7 or the overbased sulfurized alkylphenol of Comparative Example 3 and 100 millimoles of calcium per kg of additive package from the sulfonate, the remainder being base oil. The additive packages were poured into a glass flask and stored at 20° C. To test the compatibility of the package at 80° C., packages were exposed to the following daily heating cycle: 80° C. for 8 hours and 14 hours at 20° C. The test was run for 28 days and evaluated at the end of this time period. Ratings were the same as for Compatibility Test 1. The results of this test are set forth below in Table 4.

TABLE 4

| Performance Test | Example 7 | Example 7 | Comparative Example 3 | Comparative Example 3 |
|---|---|---|---|---|
| Compatibility Test 1 | 20° C. | 80° C. | 20° C. | 80° C. |
| additive package | 2 | 2 | 2 | 2 |
| additive package + oil | 2 | 2 | 2 | 2 |
| Compatibility Test 2 | 20° C. | 80° C. | 20° C. | 80° C. |
| additive package | 2 | 2 | 2 | 2 |

0 = free of sediment
1 = hazy
2 = sediment present
3 = gelled

Komatsu Hot Tube (KHT) Test

The lubricating oil compositions of Example 9 and Comparative Example 5 were evaluated in a Komatsu Hot Tube (KHT) Test. A lubricating oil composition is passed through a temperature-controlled glass tube for a period of time by employing a suitable air flow. The temperature of the test was 290° C. and the test was run for 16 hours. The glass tube is then cooled and washed, and the color of any lacquer deposition remaining on the inner surface of the glass tube is determined using a color merit rating ranging from 0 to 10 (0=black and 10=clean). In cases in which the glass tubes are completely blocked with deposits, the test result is recorded as "blocked". The results of the Komatsu hot tube test are set forth below in Table 5.

Dispersion Test

The lubricating oil compositions of Example 9 and Comparative Example 5 were evaluated in a dispersion test. This test evaluates the ability of the oils to keep asphaltenic and carbonaceous materials dispersed by measuring the dispersion of oil and black matter on filter paper. Dispersions are measured on both fresh and aged oils, with different treatment heating conditions and with and without water addition.

The fresh sample consisted of a mixture of a majority of a lubricating oil composition and carbon black. The aged sample consisted of a mixture of fresh lubricating oil composition which is aged by heating at elevated temperature under oxidizing conditions. Carbon black is added to the aged sample after the aging step.

Both fresh and aged oil samples are then subjected to three different heat treatments, both with and without water addition, making a total of six different treatments. A drop of treated sample is then placed on a piece of filter paper and developed in an incubator for 48 hours. After development, the drops form a small, dark circular sludge area surrounded by a light oil area. The diameters of the oil and sludge areas are measured and the ratio of the oil:sludge diameters calculated. The test results are reported as 6x, which is the sum of the ratio of oil:sludge diameters from the six different treatments. The results of the dispersion test are set forth below in Table 5.

TABLE 5

| Performance Test | Example 9 | Comparative Example 5 |
|---|---|---|
| Komatsu Hot Tube Test | 8 | 8 |
| Dispersion Test | 489/600 | 492/600 |

Lubricating Oil Low Temperature Viscosity Performance

The low temperature viscosity properties of the overbased salt of an oligomerized alkylphenol of Example 7 were compared to the overbased sulfurized alkylphenol of Comparative Example 3 in a 5W30 oil and a 5W40 oil.

The 5W30 oil contained (a) 3 wt. % of an oil concentrate of a borated bis-succinimide dispersant; (b) 5 wt. % of an oil concentrate of a ethylene carbonate-treated bis-succinimide dispersant; (c) 1.36 wt. % of an oil concentrate of a low overbased calcium sulfonate; (d) 0.4 wt. % of an oil concentrate of a salt of terephthalic acid and a bis-succinimide dispersant; (e) 1.08 wt. % of an oil concentrate of a secondary zinc dithiophosphate anti-wear agent; (f) 0.4 wt. % of an oil concentrate of a molybdenum oxysulfide complex of a mono-succinimde dispersant; (g) 0.5 wt. % of an alkylated diphenylamine oxidation inhibitor; (h) 0.5 wt. % of a phenolic antioxidant; (i) 30 ppm of a foam inhibitor; and (j) the balance being a mixture of Group III base oils. The overbased salt of an oligomerized alkylphenol of Example 7 and the overbased sulfurized alkylphenol of Comparative Example 3 were added to the 5W30 oil on an equal calcium basis. The weight percent of the overbased salt of an oligomerized alkylphenol of Example 7 after addition to the 5W30 oil was 2.32 wt %. The weight percent of the overbased sulfurized alkylphenol of Comparative Example 3 after addition to the 5W30 oil was 2.37 wt. %.

The 5W40 oil contained (a) 3 wt. % of an oil concentrate of a borated bis-succinimide dispersant; (b) 5 wt. % of an oil concentrate of a ethylene carbonate-treated bis-succinimide dispersant; (c) 1.36 wt. % of an oil concentrate of a low overbased calcium sulfonate; (d) 0.4 wt. % of an oil concentrate of a salt of terephthalic acid and a bis-succinimide dispersant; (e) 1.08 wt. % of an oil concentrate of a secondary zinc dithiophosphate anti-wear agent; (f) 0.4 wt. % of an oil concentrate of a molybdenum oxysulfide complex of a mono-succinimde dispersant; (g) 0.5 wt. % of an alkylated diphenylamine oxidation inhibitor; (h) 0.5 wt. % of a phenolic antioxidant; (i) 30 ppm of a foam inhibitor; and (j) the balance being a mixture of Group III base oils. The overbased salt of an oligomerized alkylphenol of Example 7 and the overbased sulfurized alkylphenol of Comparative Example 3 were added to the 5W40 oil on an equal calcium basis. The weight percent of the overbased salt of an oligomerized alkylphenol of Example 7 after addition to the 5W40 oil was 2.32 wt %. The weight percent of the overbased sulfurized alkylphenol of Comparative Example 3 after addition to the 5W40 oil was 2.37 wt. %.

The low temperature viscosity properties of the finished 5W30 and 5W40 oils were evaluated using the ASTM D4684 Mini-Rotary Viscometer (MRV) test.

ASTM D4684 Mini-Rotary Viscometer (MRV) Test

In this test, a test oil is first heated, and then cooled to test temperature, in this case −35° C., in a mini-rotary viscometer cell. Each cell contains a calibrated rotor-stator set, in which the rotor is rotated by means of a string wound around the rotor shaft and attached to a weight. A series of increasing weights are applied to the string starting with a 10 g weight until rotation occurs to determine the yield stress. The results are reported as Yield Stress as<the applied force in Pascals. A 150 g weight is then applied to determine the apparent viscosity of the oil. The larger the apparent viscosity, the more likely it is that the oil will not be continuously and adequately supplied to the oil pump inlet. The results are reported as Viscosity in centipoise.

The results of the MRV test for the 5W30 and 5W40 oils are set forth below in Tables 6 and 7, respectively.

TABLE 6

5W30 OIL

| Performance Test MRV | Example 7 | Comparative Example 3 |
|---|---|---|
| Yield stress | 0 < Y <= 35 | 0 < Y <= 35 |
| Viscosity | 18512 | 18224 |

TABLE 7

5W40 OIL

| Performance Test MRV | Example 7 | Comparative Example 3 |
|---|---|---|
| Yield stress | 0 < Y <= 35 | 0 < Y <= 35 |
| Viscosity | 33946 | 36225 |

Corrosion Test

ASTM D6594-06 corrosion test was used to evaluate the corrosive properties of a test oil containing the overbased salt of an oligomerized alkylphenol of Example 7 and the overbased sulfurized alkylphenol of Comparative Example 3. In this test, a metal test tube of lead (Pb), tin (Sn), or copper (Cu) was placed in an oil at an elevated temperature (135° C.) for 168 hours with a constant air flow. The amount of corrosion is given in parts per million (ppm) of metal in the oil. The lubricating oil compositions used were the same as described above for the 5W30 oil in the lubricating oil low temperature performance test. The results of the corrosion test are set forth below in Table 8.

TABLE 8

| Performance Test Corrosion test | Example 7 | Comparative Example 3 |
|---|---|---|
| Pb (ppm) | 78 | 106 |
| Cu (ppm) | 9 | 9 |
| Sn (ppm) | 1 | 1 |

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. An overbased salt of an oligomerized alkylhydroxyaromatic compound, wherein the alkyl group of the alkylhydroxyaromatic compound is derived from an olefin mixture comprising propylene oligomers having an initial boiling point of at least about 195° C. and a final boiling point of greater than 325° C. and up to about 400° C. as measured by ASTM D86.

2. The overbased salt of claim 1, wherein the propylene oligomers have an initial boiling point of at least about 220° C. as measured by ASTM D86.

3. The overbased salt of claim 1, wherein the propylene oligomers have a final boiling point of about 330° C. to about 375° C. as measured by ASTM D86.

4. The overbased salt of claim 1, wherein the propylene oligomers have an initial boiling point of at least about 220° C. and a final boiling point of about 330° C. to about 375° C. as measured by ASTM D86.

5. The overbased salt of claim 1, wherein the propylene oligomers contain a distribution of carbon atoms that comprise at least about 50 weight percent of $C_{14}$ to $C_{20}$ carbon atoms.

6. The overbased salt of claim 1, wherein the propylene oligomers comprise at least about 1 wt. % $C_{27+}$ and up to about 5 wt. % $C_{27+}$ carbon atoms.

7. The overbased salt of claim 1, wherein the salt is an alkali or alkaline earth metal salt.

8. The overbased salt of claim 1, wherein the oligomerized alkyl hydroxyaromatic compound is a sulfurized alkylhydroxyaromatic compound.

9. The overbased salt of claim 1, wherein the hydroxyaromatic, compound is a phenol and the olefin mixture comprises propylene pentamers, hexamers, heptamers, octamers, nonamers, or mixtures thereof.

10. A process for preparing an overbased salt of an oligomerized alkylhydroxyaromatic compound, the process comprising the steps of:
  (a) alkylating a hydroxyaromatic compound with an olefin mixture comprising propylene oligomers having an initial boiling point of at least about 195° C. and a final boiling point of greater than 325° C. and up to about 400° C. as measured by ASTM D86, to provide an alkylhydroxyaromatic compound;
  (b) neutralizing the alkylhydroxyaromatic compound of step (a) to provide a salt of the alkylhydroxyaromatic compound;

(c) oligomerizing the salt of the alkylhydroxyaromatic compound of step (b) to provide a salt of an oligomerized alkylhydroxyaromatic compound; and (d) overbasing the salt of the oligomerized alkylhydroxyaromatic compound of step (c) to provide the overbased salt of the oligomerized alkylhydroxyaromatic compound.

11. The process of claim 10, wherein the propylene oligomers have an initial boiling point of at least about 220° C. and a final boiling point of about 330° C. to about 375° C. as measured by ASTM D86.

12. The process of claim 10, wherein the propylene oligomers contain a distribution of carbon atoms that comprise at least about 50 weight percent of $C_{14}$ to $C_{20}$ carbon atoms and at least about 1 wt. % $C_{27+}$ carbon atoms.

13. A lubricating oil composition comprising (a) a major amount of an oil of lubricating viscosity; and (b) an overbased salt of an oligomerized alkylhydroxyaromatic compound, wherein the alkyl group of the alkylhydroxyaromatic compound is derived from an olefin mixture comprising propylene oligomers having an initial boiling point of at least about 195° C. and a final boiling point of greater than 325° C. and up to about 400° C. as measured by ASTM D86.

14. The lubricating oil composition of claim 13, wherein the propylene oligomers have an initial boiling point of at least about 220° C. as measured by ASTM D86.

15. The lubricating oil composition of claim 13, wherein the propylene oligomers have a final boiling point of about 330° C. to about 375° C. as measured by ASTM D86.

16. The lubricating oil composition of claim 13, wherein the propylene oligomers contain a distribution of carbon atoms that comprise at least about 50 weight percent of $C_{14}$ to $C_{20}$ carbon atoms and at least about 1 wt. % $C_{27+}$ carbon atoms.

17. The lubricating oil composition of claim 13, wherein the overbased salt is present in the lubricating oil composition in an amount of about 0.01 wt. % to about 40 wt. %, based on the total weight of the composition.

18. A method for reducing the endocrine disrupting properties of a lubricating oil composition on exposure to mammals, the method comprising adding the overbased salt of the oligomerized alkylhydroxyaromatic compound of claim 1 to a lubricating oil composition comprising a major amount of an oil of lubricating viscosity.

* * * * *